(12) United States Patent
Raymond et al.

(10) Patent No.: US 8,118,429 B2
(45) Date of Patent: Feb. 21, 2012

(54) SYSTEMS AND METHODS OF PHASE DIVERSITY WAVEFRONT SENSING

(75) Inventors: Thomas D. Raymond, Edgewood, NM (US); Paul Pulaski, Albuquerque, NM (US); Stephen W. Farrer, Albuquerque, NM (US); Daniel R. Neal, Tijeras, NM (US); Alan H. Greenaway, Edinburgh (GB); David M. Faichnie, Glasgow (GB); Heather I. Campbell Dalgarno, West Lothian (GB); Graham N. Craik, Edinburgh (GB)

(73) Assignee: AMO Wavefront Sciences, LLC., Santa Ana, CA (US)

( * ) Notice: Subject to any disclaimer, the term of this patent is extended or adjusted under 35 U.S.C. 154(b) by 471 days.

(21) Appl. No.: 12/259,381

(22) Filed: Oct. 28, 2008

(65) Prior Publication Data

US 2009/0185132 A1    Jul. 23, 2009

Related U.S. Application Data

(60) Provisional application No. 60/983,380, filed on Oct. 29, 2007, provisional application No. 61/028,877, filed on Feb. 14, 2008, provisional application No. 61/048,042, filed on Apr. 25, 2008.

(51) Int. Cl.
*A61B 3/10* (2006.01)
*G02B 5/18* (2006.01)

(52) U.S. Cl. ............... 351/205; 351/213; 359/566

(58) Field of Classification Search ............ 359/15, 359/565, 569, 566, 663; 356/512; 351/161, 351/168, 205, 206, 213, 221
See application file for complete search history.

(56) References Cited

U.S. PATENT DOCUMENTS

| | | | |
|---|---|---|---|
| 5,598,261 | A  | 1/1997  | Duncan et al. |
| 6,107,617 | A  | 8/2000  | Love et al. |
| 6,439,720 | B1 | 8/2002  | Graves et al. |
| 6,975,457 | B1 | 12/2005 | Greenway et al. |
| 7,232,999 | B1 | 6/2007  | Otten et al. |
| 7,419,264 | B1 | 9/2008  | Otten, III et al. |

(Continued)

FOREIGN PATENT DOCUMENTS

WO    WO 00/17612    3/2000

(Continued)

OTHER PUBLICATIONS

W. Neil Charman et al; "Can we measure wave aberration in patients with diffractive IOLs?" Journal of Cataract & Refractive Surgery No. 11 p. 1997 (Nov. 2007).

(Continued)

*Primary Examiner* — Ricky Mack
*Assistant Examiner* — Mahidere Sahle
(74) *Attorney, Agent, or Firm* — AMO Wavefront Sciences, LLC.

(57) ABSTRACT

A phase diversity wavefront sensor includes an optical system including at least one optical element for receiving a light beam; a diffractive optical element having a diffractive pattern defining a filter function, the diffractive optical element being arranged to produce, in conjunction with the optical system, images from the light beam associated with at least two diffraction orders; and a detector for detecting the images and outputting image data corresponding to the detected images. In one embodiment, the optical system, diffractive optical element, and detector are arranged to provide telecentric, pupil plane images of the light beam. A processor receives the image data from the detector, and executes a Gerchberg-Saxton phase retrieval algorithm to measure the wavefront of the light beam.

9 Claims, 19 Drawing Sheets

U.S. PATENT DOCUMENTS

2006/0173328 A1 8/2006 Fan et al.
2007/0183647 A1 8/2007 Allman et al.
2010/0276573 A1* 11/2010 Duerksen .................. 250/208.6

FOREIGN PATENT DOCUMENTS

WO 2004113856 A1 12/2004

OTHER PUBLICATIONS

Blanchard et al.; "Simultaneous Multi-plane Imagin with a Distorted Diffraction Grating" Applied Optics (1999).

Slimane Djidel; "High Speed, 3-Dimensional, Telecentric Imaging." 14 Optics Express No. 18 (Sep. 4, 2006).

W. Neil Charman et al., "Can we measure wave aberration in patients with diffractive IOLs?," 33 Journal of Cataract & Refractive Surgery No. 11, p. 1997 (Nov. 2007).

Blanchard, P.B and Greenaway, A.H., "Simultaneous Multi-plane Imaging with a Distorted Diffraction Grating," Applied Optics (1999).

Slimane Djidel, "High Speed, 3-Dimensional, Telecentric Imaging," 14 Optics Express No. 18 (Sep. 4, 2006) pp. 8269-8277.

Ian Grant et al. "Confidence Interval Estimates in PIV Measurements of Turbulent Flows," Applied Optics, vol. 29, No. 10, Apr. 1, 1990, pp. 1400-1405.

Fernando Diaz-Douton et al. "Curvature sensor for ocular wavefront measurement," Optics Letters, Aug. 1, 2006, vol. 31, No. 15, pp. 2245-2247.

D. M. Cuevas et al., "Distored Grating Wavefront Sensor and Ophthalmic Applications," 5th International Workshop on Adaptive Optics for Industry and Medicine, (2005) pp. 1-11.

Michael Teague, "Deterministic phase retrieval: a Green's function solution," J. Opt. Soc. Am., vol. 73, No. 11, Nov. 1983, pp. 1434-1441.

* cited by examiner

SYSTEMS AND METHODS OF PHASE DIVERSITY WAVEFRONT SENSING

CROSS-REFERENCES TO RELATED APPLICATIONS

This patent application claims the priority benefit under 35 U.S.C. §119(e) from U.S. provisional patent application 60/983,380 filed on 30 Oct. 2007, U.S. provisional patent application 61/028,877 filed on 14 Feb. 2008, and U.S. provisional patent application 61/048,042 filed on 25 Apr. 2008, each filed in the names of Thomas D. Raymond et al., the entirety of each of which is hereby incorporated herein by reference for all purposes as if fully set forth herein.

BACKGROUND AND SUMMARY

1. Field

This invention pertains to the field of wavefront measurements, and more particularly to systems and methods of measuring a wavefront of light using a phase diversity wavefront sensor.

2. Description

A number of systems and methods have been developed for measuring a wavefront of light. Such wavefront measurements have been employed in a number of applications, including ophthalmic applications such as measuring aberrations of an eye, and measuring surfaces of objects such as contact lenses.

One wavefront sensor that has been employed in a number of systems for various wavefront sensing applications is the Shack Hartmann wavefront sensor (SHWS). A SHWS includes an array of lenslets which image focal spots onto a detector array. SHWS's have been employed in a variety of ophthalmic and metrological applications.

However, a SHWS has some limitations in certain applications.

For example, with a SHWS, the wavefront is expected to produce a single local tilt. In general, an SHWS has difficulty measuring wavefronts with discontinuities. However, in some applications, and particularly in some ophthalmic applications, the wavefront may have multiple tilts, which may produce multiple focal spots. For example, such discontinuities can be produced by multi-focal optical devices, including multifocal contact lenses and multifocal intraocular lenses (IOL). W. Neil Charman et al., "*Can we measure wave aberration in patients with diffractive IOLs?,*" 33 JOURNAL OF CATARACT & REFRACTIVE SURGERY No. 11, p. 1997 (November 2007) discusses some problems in using a SHWS to make wavefront measurements of a patient with a diffractive IOL. Charman notes that when a measurement is taken on an eye that has been implanted with a diffractive IOL, the lenslets of the SHWS will produce multiple images and the detector will record multiple overlapping spot patterns. So, it is difficult at best for a SHWS to measure wavefronts produced by multi-focal optical elements, such as diffractive IOLs.

Another limitation of the SHWS pertains to its limited dynamic range. For example, to measure ophthalmic aberrations of a human eye over the wide range presented by the human population, as a practical matter one needs to employ an adjustable optical system in conjunction with the SHWS so that operation of the SHWS can be maintained within its dynamic range. This can add to the complexity and cost of the measurement system, and requires alignment that can reduce the measurement precision of the instrument.

Another type of wavefront sensor is a phase diversity wavefront sensor (PDWS), also sometimes referred to as a curvature sensor. A PDWS may be used to analyze wavefronts at two or more planes that are generally orthogonal to the direction of propagation of an optical beam. In general, a PDWS measurement system makes measurements via an optical system that is capable of imaging two or more planes at once, to minimize or eliminate the effects of any time-varying changes in the optical beam. Graves et al. U.S. Pat. No. 6,439,720 describes a measurement system that includes a PDWS. Early PDWS systems employed a relatively complex arrangement of beam splitters and/or optical delays to generate the necessary images.

In 1999, Blanchard, P. B and Greenaway, A. H., "*Simultaneous Multi-plane Imaging with a Distorted Diffraction Grating,*" APPLIED OPTICS (1999) ("Blanchard") disclosed the use of a diffractive optical element (DOE) in a PDWS. As disclosed by Blanchard, the DOE uses local displacement of lines in a diffraction grating to introduce arbitrary phase shifts into wavefronts diffracted by the grating into the non-zero orders to create multiple images of the incident light. In Blanchard's arrangement, a diffraction grating having a quadratic displacement function is employed in conjunction with a collocated single lens to alter the optical transfer function associated with each diffraction order such that each order has a different degree of defocus. Greenaway et al. U.S. Pat. No. 6,975,457 and Greenaway et al. U.S. Patent Application Publication 2006/0173328 describe further details of a PDWS that includes a DOE.

Otten III et al. U.S. Pat. No. 7,232,999 discloses the use of a PDWS with a DOE for determining the characteristics of an infrared wavefront produced by a laser. Slimane Djidel, "*High Speed, 3-Dimensional, Telecentric Imaging,*" 14 OPTICS EXPRESS No. 18 (4 Sep. 2006) describes design, testing and operation of a system for telecentric imaging of dynamic objects with a single lens system. However, the procedure described therein is not extensible to more complicated configurations.

Nevertheless, these references are not generally directed to applications where there is speckle and/or discontinuities or large aberrations in the wavefront, such as may be the case in many ophthalmic applications, including the measurement of IOLs, multifocal contact lenses, etc., and eyes or optical systems that include such devices. Furthermore, these references do not provide a generalized design method for incorporating a PDWS into more complicated optical systems.

It would be desirable to provide an ophthalmic measurement instrument that utilizes the benefits of a PDWS, alone or in conjunction with a SHWS. It would further be desirable to provide such an instrument that can measure wavefronts with speckle and/or discontinuities or large aberrations in the wavefront. More particularly, it would be desirable to provide such an instrument that can perform wavefront measurements for systems that include a multifocal element, such as an intraocular or contact lens that is either a refractive multifocal lens, a diffractive multifocal lens, or a diffractive monofocal lens. It would also be desirable to provide a generalized method of designing a measurement system including a PDWS.

In one aspect of the invention, a phase diversity wavefront sensor comprises: an optical system including at least one optical element for receiving a light beam; a diffractive optical element having a diffractive pattern defining a filter function, the diffractive optical element being arranged to produce, in conjunction with the optical system, images from the light beam associated with at least two diffraction orders; and a detector for detecting the images and outputting image data corresponding to the detected images, wherein the optical system, diffractive optical element, and detector are arranged to provide telecentric, pupil plane images of the light beam.

In another aspect of the invention, a method is provided for measuring a wavefront of an optical system including a multifocal element. The method comprises: providing a light beam to a lens, the lens being a refractive multifocal lens, a diffractive multifocal lens, or a diffractive monofocal lens; directing light from the lens to a phase diversity wavefront sensor, comprising an optical system including at least one optical element for receiving a light beam, and a diffractive optical element the shape of which is defined by a filter function, the diffractive optical element being arranged to produce in conjunction with the optical system images of the light beam associated with at least two diffraction orders; and a detector for detecting the images and outputting image data corresponding to the detected images; and measuring the wavefront of the light from the lens using the image data output by the detector.

In yet another aspect of the invention, a method is provided for measuring a wavefront of an object having first and second surfaces. The method comprises: providing a light beam to the object; directing light from the lens to a phase diversity wavefront sensor, the lens being a refractive multifocal lens, a diffractive multifocal lens, or a diffractive monofocal lens, the phase diversity wavefront sensor comprising an optical system including at least one optical element for receiving a light beam, and a diffractive optical element the shape of which is defined by a filter function, the diffractive optical element being arranged to produce in conjunction with the optical system images of the light beam associated with at least two diffraction orders; and a detector for detecting the images and outputting image data corresponding to the detected images; and simultaneously measuring the first and second surfaces of the object using the image data output by the detector.

In still another aspect of the invention, a method is provided for designing a phase diversity wavefront sensor. The method comprises: providing one or more analytic solutions for paraxial equations that govern an optical configuration of the phase diversity wavefront sensor; providing a set of input design parameters for the phase diversity wavefront sensor; generating a set of output values from the analytical solutions and the input design parameters; and determining whether the output parameters meet a viability threshold.

In a further aspect of the invention, a phase diversity wavefront sensor comprises: an illuminating optical system for delivering light onto a retina of an eye; a receiving optical system for receiving light reflected by the retina, the receiving optical system comprising a diffractive optical element including a diffraction pattern defining a filter function, the diffractive optical element being arranged to produce, in conjunction with the optical system, at least two images from the light beam associated with at least two diffraction orders; a detector for detecting the at least two images; a memory containing instructions for executing a Gerchberg-Saxton phase retrieval algorithm on data produced by the detector in response to the detected images; and a processor configured to execute the Gerchberg-Saxton phase retrieval algorithm so as to characterize a wavefront produced by the reflected light.

DETAILED DESCRIPTION

Figure 1:
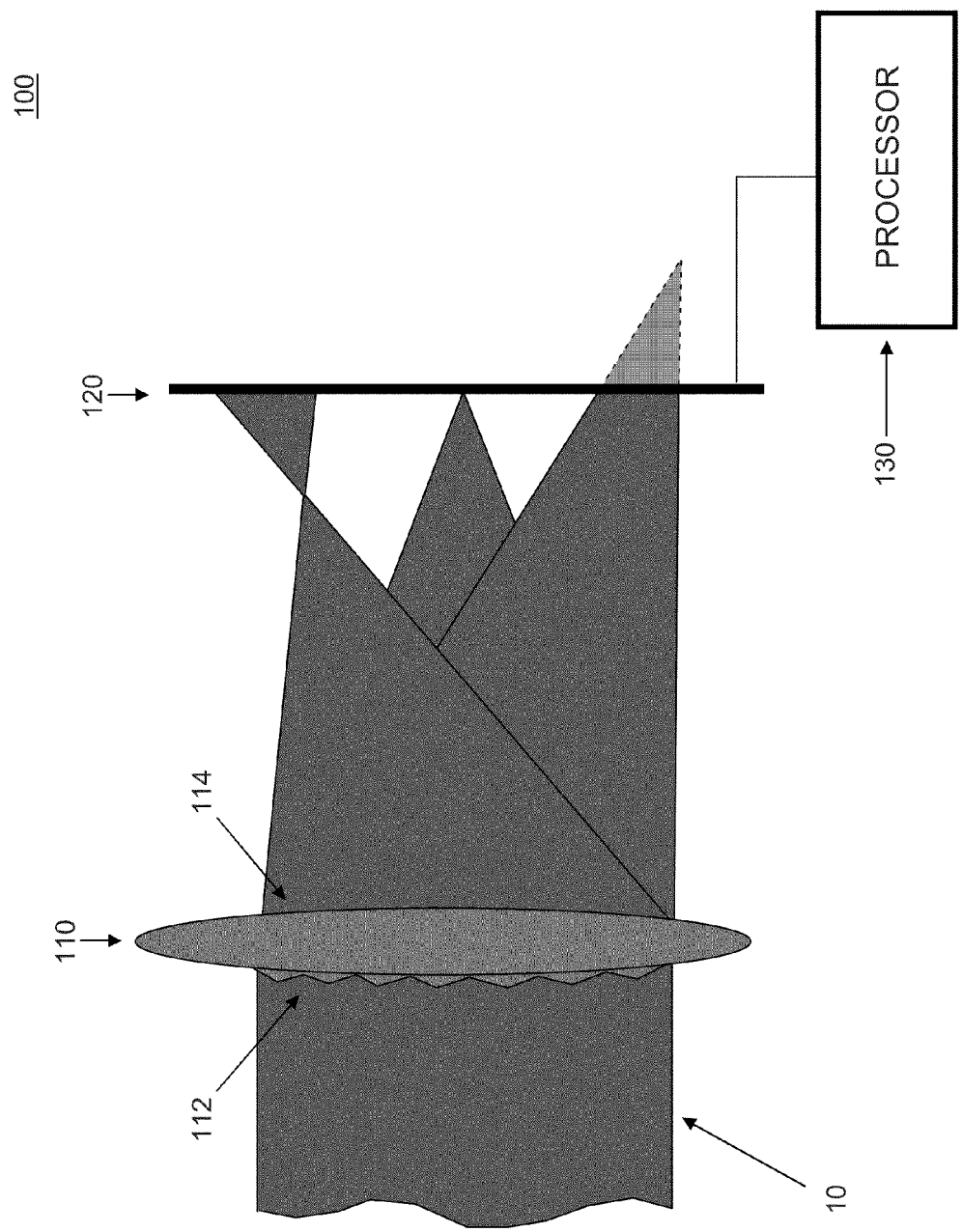
FIG. 1 illustrates the use of a diffractive optical element (DOE) in a phase diversity wavefront sensor (PDWS).

FIG. 1 illustrates the use of a diffractive optical element (DOE) in a phase diversity wavefront sensor (PDWS) 100. PDWS 100 includes an optical element 110, a detector 120, and a processor 130. Optical element 110 includes a diffractive optical element (DOE) (e.g., a diffraction grating) 112 collocated with optical element 114 with positive focal power. Although shown in transmission mode, optical element 110 may alternately be used in reflection where diffraction grating 114 is collocated with optical element 114 comprising a mirror.

In the illustrated embodiment, optical element 114 is a lens, and diffractive grating 112 is disposed on a surface of lens 114. Alternatively, diffractive grating 112 may be incorporated inside lens 114 or be formed from the material used to form lens 114. In some embodiments, lens 114 and diffractive grating 112 form a single DOE, where lens 114 is itself a DOE, for example, disposed on a same surface or an opposite surface as diffractive grating 112. In yet other embodiments, lens 114 and grating 112 are separate elements that touch one another or are separated by a relatively small distance. Element 114 could be refractive, diffractive or reflective.

Detector 120 may be a charge coupled device (CCD).

In one embodiment, diffraction grating 112 is distorted by a quadratic filter function so that optical element 110 introduces an optical power that depends upon the diffraction order. Optical element 110 produces angularly displaced beams with different focal power. The combination of diffraction grating 112 and lens 114 yields a net optical power given by:

$$P = \frac{1}{f_{TOTAL}} = \frac{1}{f} + \frac{R^2}{2mW_{20}} = P_{LENS} + P_{GRATING} \quad (1)$$

where m is the diffraction order of diffraction grating 112, R=the aperture radius of diffraction grating 112 and $W_{20}$ is a standard defocus term specifying the phase shift from center to edge of the optic. This is related to the quadratic distortion in the grating as specified by Blanchard. Note that the grating period in such distorted gratings is not constant, but can still be specified in terms of an average period at the DOE center. This grating period is the average distance between the lines in the grating and, together with the wavelength of the incident light, determines the diffraction angle of the diffracted beams, and hence their separation on the detector array.

In one embodiment, diffraction grating 112 is distorted by a filter function that is non-quadratic and has non-mixed symmetry.

In the case of illumination of DOE 110 by plane wave 10, it is clear that each order produces a focus on either side of the detector plane.

Figure 2:
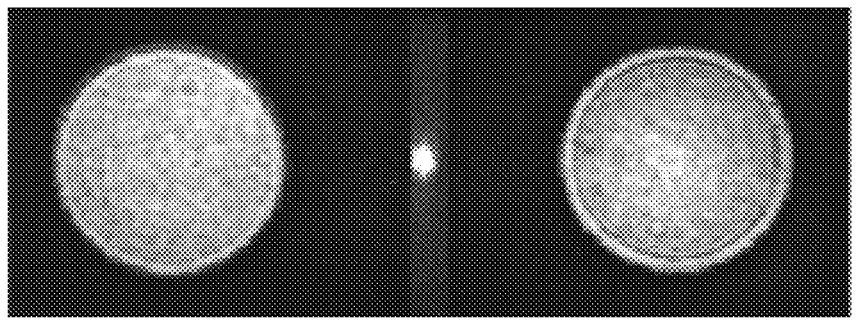
FIG. 2 illustrates an intensity image produced by the PDWS of FIG. 1.

In PDWS 100, detector 120 is located at the focal plane for the $0^{th}$ order beam and is referred to as an "image plane PDWS." In that case, FIG. 2 illustrates an intensity image produced by PDWS 100. This arrangement produces a real image at the +1 diffraction order, a virtual image at the −1 diffraction order, and a far field pattern at the 0 diffraction pattern. As can be seen in FIG. 2, this produces a bright spot $0^{th}$ order beam, and dimmer spots for the +1 and −1 diffraction orders.

Data acquisition may be accomplished by two-dimensional digitization of the intensity image at detector 120. The image data is then supplied to processor 130 for further analysis to measure the wavefront of plane wave 10.

Figure 3:
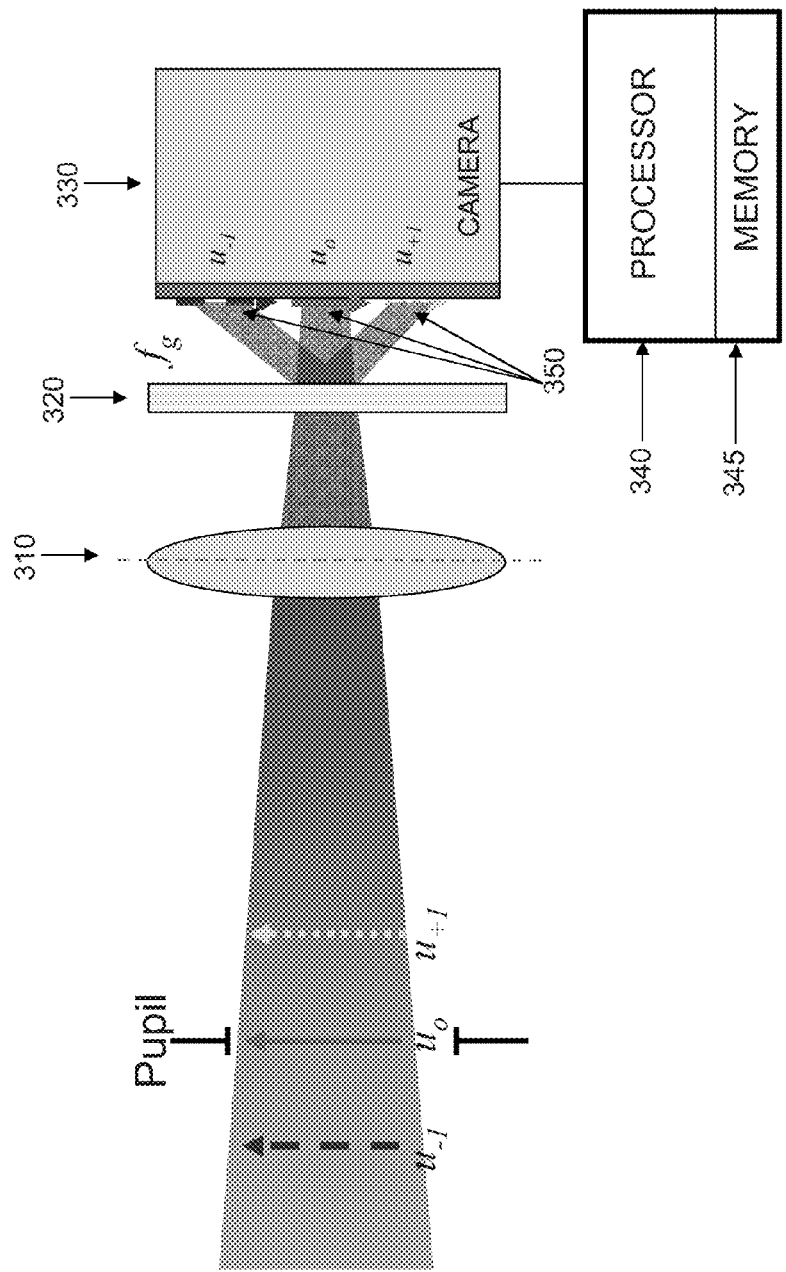
FIG. 3 illustrates another configuration of a PDWS.

FIG. 3 illustrates another configuration of a PDWS 300. PDWS 300 comprises an optical element (e.g., a lens) 310, a diffractive optical element (e.g., a diffraction grating) 320, a camera or detector 330, and a processor 340. Detector 330 may comprise a charge coupled device (CCD). PDWS 300 possesses certain characteristics that may be beneficial for measuring wavefronts in ophthalmic applications, as will be discussed in greater detail below. Associated with processor 340 is memory 345 containing instructions for executing a phase retrieval algorithm on data produced by detector 330.

Figure 4:
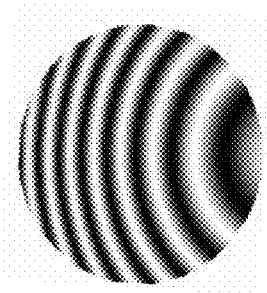
FIG. 4 illustrates one embodiment of diffraction grating.

FIG. 4 illustrates one embodiment of diffraction grating 320. In one embodiment of FIG. 4, diffraction grating 320 comprises a distorted grating that is distorted by a quadratic filter function. This is also known as an off-axis Fresnel lens.

In one embodiment, diffraction grating 320 is distorted by a filter function that is non-quadratic and has non-mixed symmetry.

Figure 5:
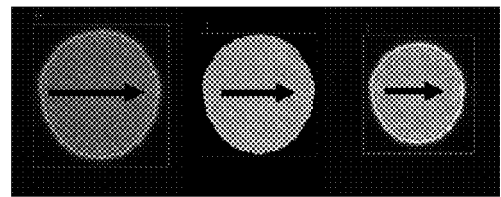
FIG. 5 illustrates an intensity image produced by the PDWS of FIG. 3.

FIG. 5 illustrates an intensity image produced by PDWS 300. In contrast to PDWS 100, which is an example of an Image Plane PDWS, PDWS 300 forms real images of the beam at both sample planes and at the measurement plane (the Pupil Plane). Accordingly, PDWS 300 is referred to as a "Pupil Plane PDWS."

As shown in FIG. 3, PDWS 300 forms images of the beam 350 at different sample locations, and these images are laterally displaced at camera 330 so that they can be simultaneously acquired. PDWS 300 can be thought of as producing multiple object planes (also referred to as "observation planes" or "sample planes') that are imaged onto camera 330. In particular, object plane $\mu_{-1}$ is imaged onto the $-1^{th}$ order beam, object plane $\mu_0$ is imaged onto the $0^{th}$ order beam, and object plane $\mu_{+1}$ is imaged onto the $+1^{th}$ order beam at camera.

Although FIG. 3 illustrates an example with a converging beam, a collimated beam or a diverging beam may be employed in a particular application. Also, although FIG. 3 illustrates three "observation planes" it should be understood that more observation planes corresponding to additional diffraction orders can be employed and that only two observation planes are necessary in many applications. On the other hand, having a multitude of observation planes can provide a greater dynamic range, greater sensitivity, improved ability to discern waves with multiple wavefronts.

Data acquisition may be accomplished by two-dimensional digitization of the intensity values detected by camera 330. The detected intensity data may then be analyzed by processor 340 to determine the phase distribution that produces the intensity measured in all planes, as will now be explained in detail.

Knowledge of the sampled intensity profiles, the locations of the sample planes, and the wavelength of the beam are generally sufficient to determine the phasefront of the beam. One phase retrieval method that has been applied to PDWS data is to derive solutions to the Intensity Transport Equation (ITE). Phase retrieval via the ITE is fast and analytic.

Unfortunately the application of ITE analysis to highly aberrated beams may be problematic. M. R. Teague, 73 JOSA No. 11, pg. 1434 (1983) derived the ITE from the wave equation expressly for the phase retrieval problem. He showed that for a beam of intensity, I, wavefront, $\phi$, and wave number, $k=2\pi/l$, then its transverse derivatives and its axial derivative are related by:

$$k\frac{\partial I}{\partial z} = -I\nabla^2 \varphi - \nabla I \cdot \nabla \varphi \cong k\frac{I_{-1} - I_1}{z_{-1} - z_1} \quad (2)$$

where $$u(x, y) = \sqrt{I(x, y)}\, e^{i\varphi(x,y)} \quad (3)$$

Since the axial derivative is not known, it is approximated by the finite difference between the intensity measurements along the propagation direction as shown in EQN. 2 above. This approximation fails for beams with aberrations large enough to significantly change the beam size between the sample planes. As such properties may be found in beams in ophthalmic applications, the use of ITE-based phase retrieval methods is of limited utility, for example, for a PDWS employed in an ophthalmic aberrometer.

Accordingly, to increase the phase retrieval accuracy for beams with large aberrations, and thereby to provide a solution for employing PDWS 300 in ophthalmic applications—such as in an ophthalmic aberrometer—in PDWS 300 processor 340 performs a Gerchberg-Saxton (GB) phase retrieval algorithm using the intensity data from camera 330. The GS method does not require knowledge of the axial intensity derivative, but uses all intensity measurements to numerically calculate the phase front. The GS method is an iterative process where known intensity measurements are used with wave propagators to estimate the intensity and phase at the next measurement plane. Before each successive propagation step, the predicted intensity is replaced with the measured intensity.

Figure 6:
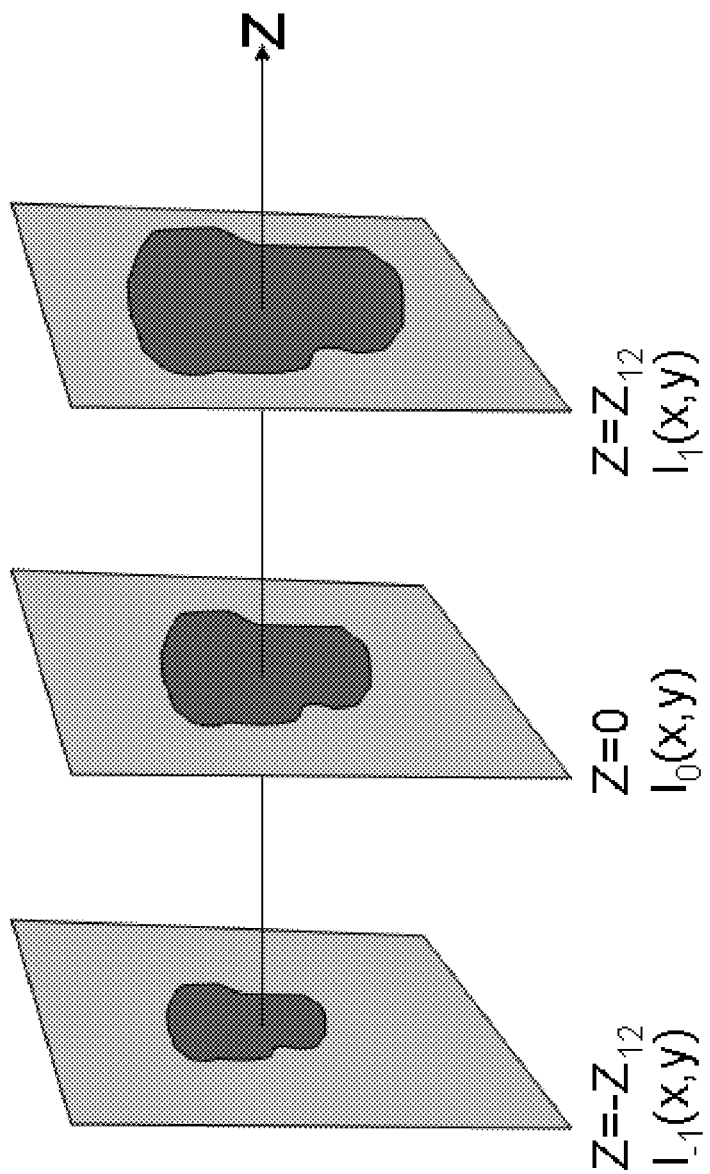
FIG. 6 illustrates operation of one embodiment of a Gerchberg-Saxton (GS) algorithm.

FIG. 6 illustrates operation of one embodiment of the GS algorithm. In a first step, processor 340 estimates, or guesses, φ(x,y). In a next step, processor 340 takes the latest estimate of φ(x,y) and propagates it to the next measurement plane. Then, processor 340 replaces the amplitude of the propagated field with the square root of the intensity measurement at that plane. Processor 340 then propagates this data to the next measurement plane, and the process is repeated for all measurement planes until the propagated intensity matches the measured sufficiently well (e.g., the difference is less than a defined threshold). If necessary, the process may proceed from the $\mu_{-1}$ measurement plane, to the $\mu_0$ measurement plane, to the $\mu_{+1}$ measurement plane, and back to the $\mu_0$ measurement plane, then to the $\mu_{-1}$ measurement plane, etc., until convergence is reached.

Figure 7:
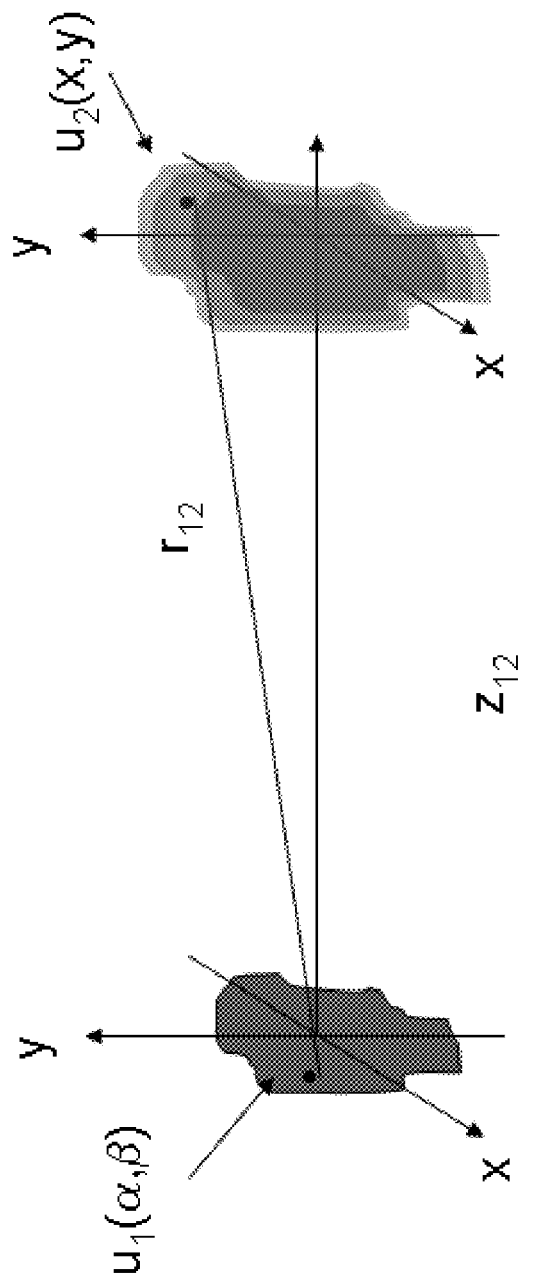
FIG. 7 illustrates propagation from one measurement plane to the next.

In one embodiment processor 340 employs a Rayleigh-Sommerfeld propagation integral to propagate from one measurement plane to the next. FIG. 7 illustrates this propagation. Given the data $\mu_1(\alpha,\beta)$ at a first measurement plane $\mu_1$, then the data is propagated to a second measurement plane, $\mu_1$, to produce propagated data $\mu_2(x,y)$ as follows:

$$u_2(x, y) = \int\int u_1(\alpha, \beta)\left(\frac{z_{12}}{i\lambda r_{12}^2}\right)e^{ikr_{12}}d\alpha d\beta \quad (4)$$

The inventors have investigated the efficacy of the iterative GS phase retrieval method in ophthalmic instruments where large dynamic range in defocus and the presence of speckle make phase retrieval with standard methods based on the intensity transport equation difficult. Simulated PDWS data covering a typical range of ophthalmic defocus aberrations with a standard PDWS configuration were generated using the Rayleigh-Sommerfeld propagation integral equation. The data was processed using the GS method and the following parameters were varied to study the robustness of the method and its rate of convergence: input pupil diameter; sample plane spacing; and irradiance characteristics. Only beams with spherical wavefronts and intensity distributions at z=0 that are zero outside a circular pupil were studied. Three intensity measurements were used. A wavelength of 635 nm was assumed. Speckled beams were simulated by imposing a random phase distribution with amplitude several radians on a uniform beam and propagating several millimeters. The size of the speckle cells of the resulting intensity distributions averaged about 1 mm.

Figure 8:
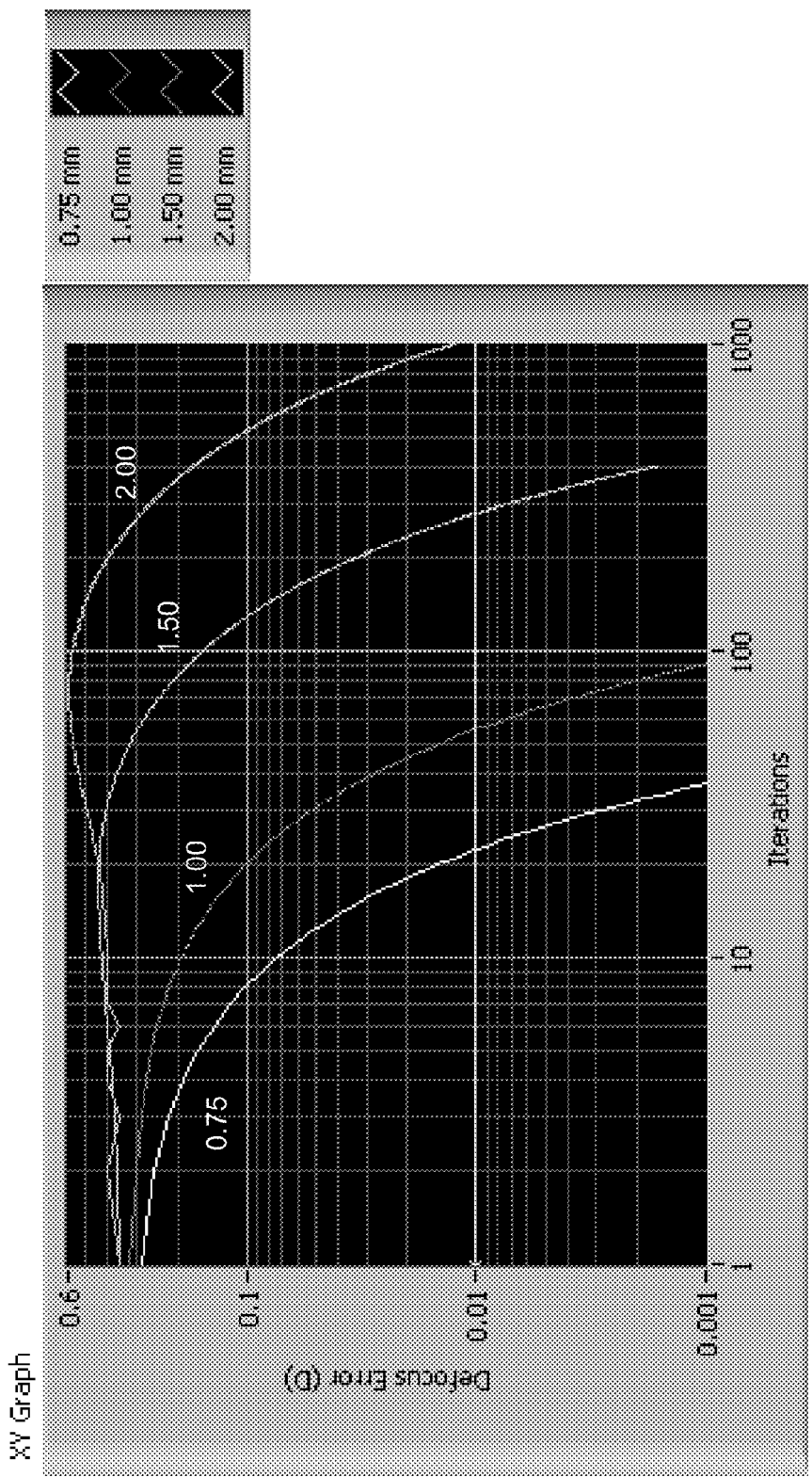
FIG. 8 illustrates the numerically calculated defocus versus iteration number in a GS algorithm for different pupil diameters.
Figure 9:
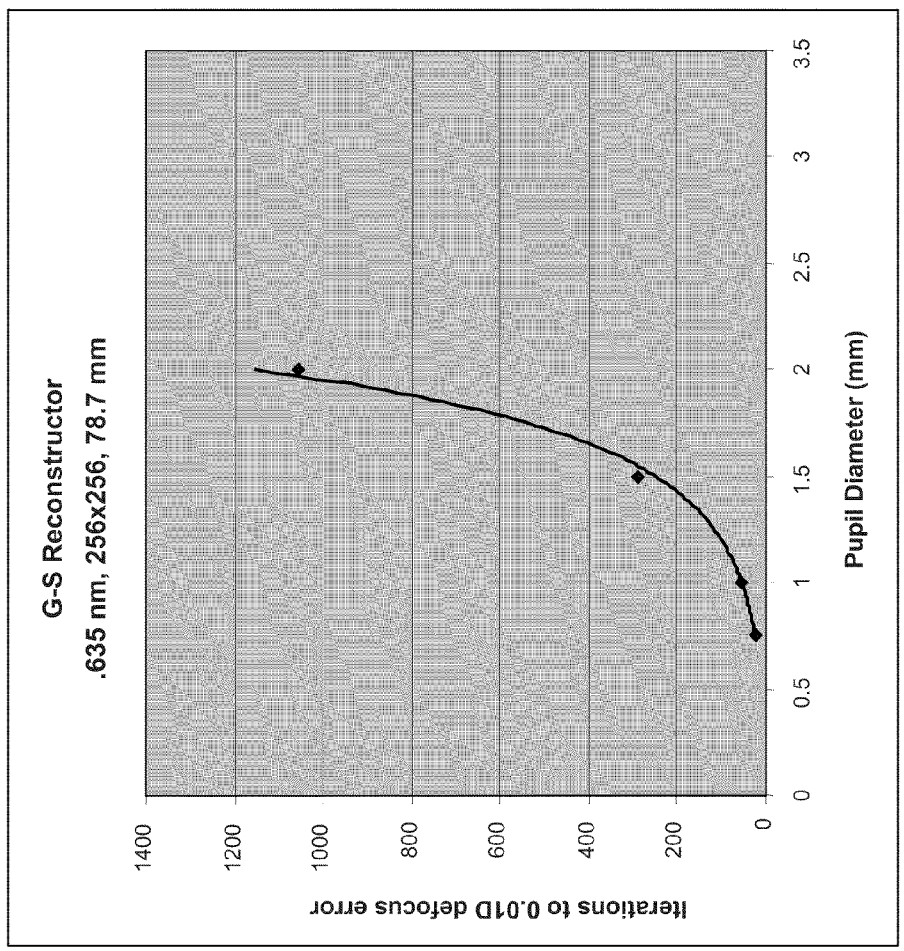
FIG. 9 plots the number of iterations in a GS algorithm required to reduce the defocus error to less than 0.01 diopters versus pupil diameter.

FIG. 8 illustrates the numerically calculated defocus versus iteration number for different pupil diameters. FIG. 9 plots the number of iterations required to reduce the defocus error to less than 0.01 diopters versus pupil diameter. FIGS. 8 and 9 show that convergence is rapid for small diameter beams but is much slower as the beam diameter increases. The number of iterations required to achieve a specified level of defocus accuracy increases approximately exponentially with input pupil diameter for fixed sample spacing.

Figure 10:
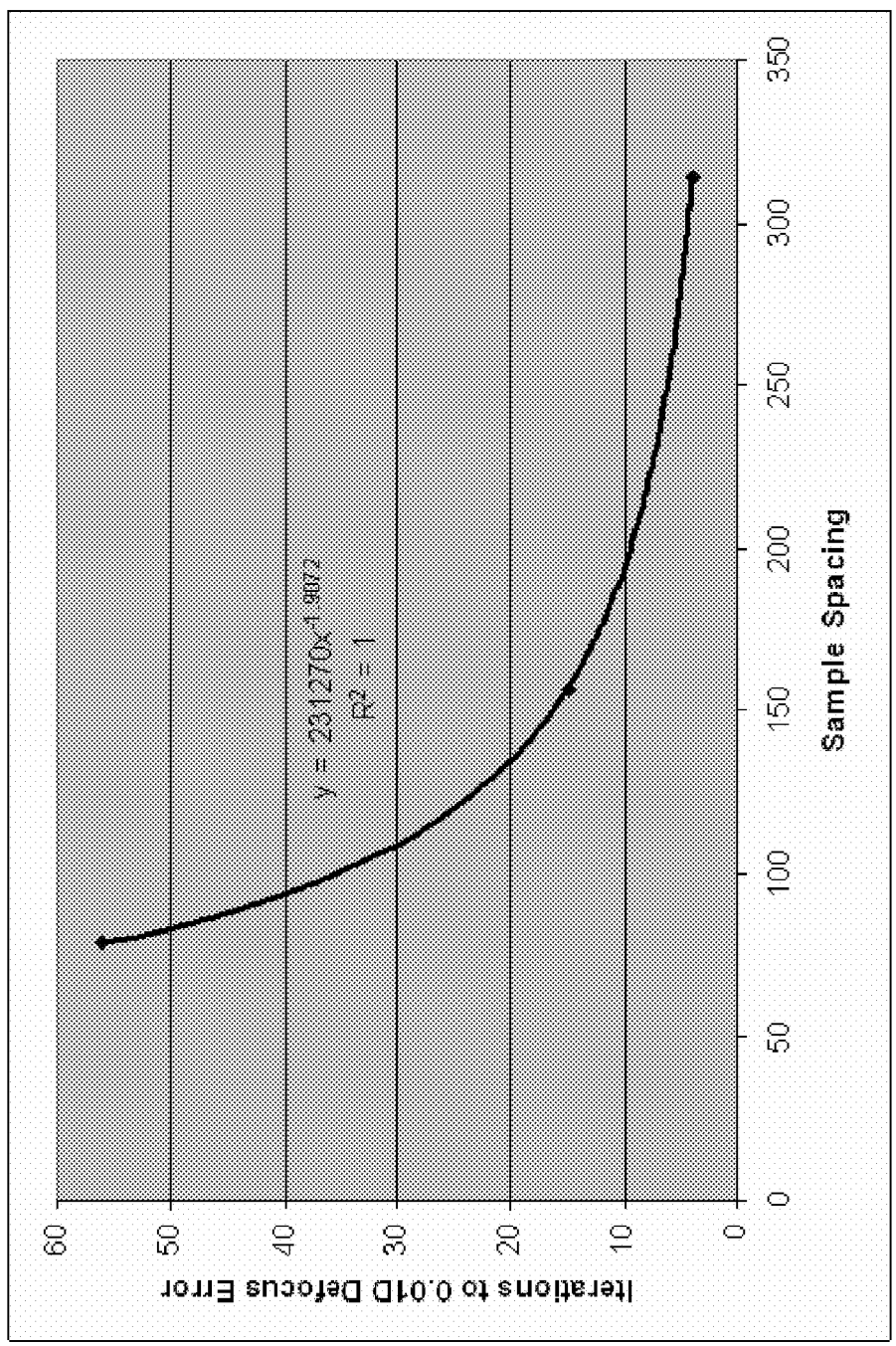
FIG. 10 plots the number of iterations in a GS algorithm required for convergence versus sample plane separation for a given beam diameter.

FIG. 10 plots the number of iterations required for convergence versus sample plane separation for a given beam diameter. It can be seen in FIG. 10 that the convergence rate improves with sample plane separation. For a given beam size, the number of iterations required to achieve a specified level of defocus accuracy decreases as the reciprocal of the sample plane spacing.

Figure 11:
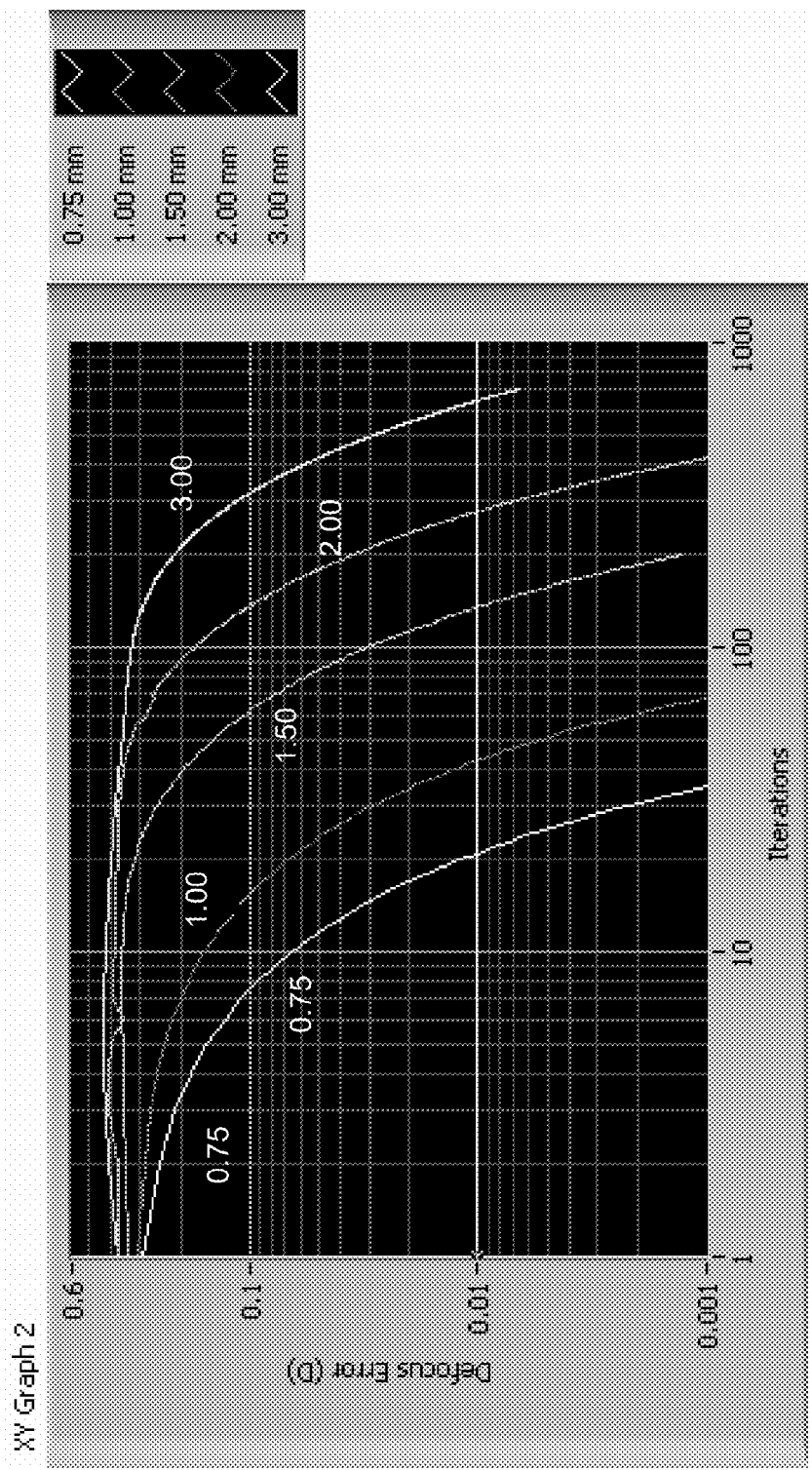
FIG. 11 illustrates the numerically calculated defocus versus iteration number in a GS algorithm for different pupil diameters in the case of an irradiance pattern where speckle is introduced.
Figure 12:
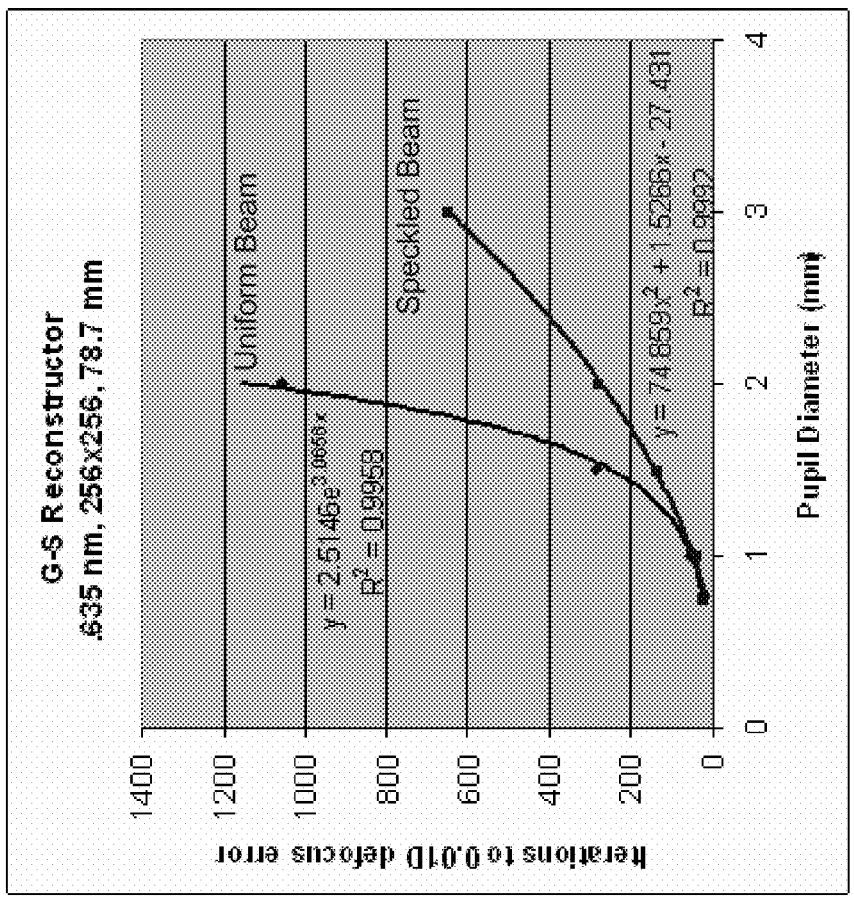
FIG. 12 plots the number of iterations required to reduce the defocus error to less than 0.01 diopters versus pupil diameter for a speckled beam, compared to a beam without speckle.

FIG. 11 illustrates the numerically calculated defocus versus iteration number for different pupil diameters in the case of an irradiance pattern where speckle is introduced. FIG. 12 plots the number of iterations required to reduce the defocus error to less than 0.01 diopters versus pupil diameter for a speckled beam (lower plot), compared to a beam without speckle (upper plot). In the case of a speckled beam, the number of iterations required to achieve a specified level of defocus accuracy increases approximately quadratically with input pupil diameter for fixed sample spacing, rather than exponentially, as is the case with beams that do not include speckle. Beneficially, for beams having relatively large beam diameters (e.g., beam diameters greater than or equal to 1.5 millimeters or greater than or equal to 2 millimeters), this significantly reduces the number of iterations required for beams containing large numbers of speckle cells, as is typical in ophthalmic aberrometers.

In PDWS 300, the dynamic range and sensitivity can be controlled by proper selection of the sample plane spacing and the number of bits of digitization of the CCD in camera 330. Meanwhile, the resolution is controlled by the magnification and the pitch of the pixels in camera 330. Beneficially, PDWS 300 provides a wide dynamic range so as to accommodate a wide range of aberrations in the input wavefront without the need to move or adjust any optical elements, thus simplifying the construction of an ophthalmic measurement instrument. Beneficially, in one embodiment PDWS 300 is capable of measuring the wavefronts of beams with at least ±3 diopters of defocus. Further beneficially, in one embodiment PDWS 300 is capable of measuring the wavefronts of beams with at least ±5 diopters of defocus. Even further beneficially, in one embodiment PDWS 300 is capable of measuring the wavefronts of beams with at least ±10 diopters of defocus.

PDWS 300 includes a number of features that are desirable for an ophthalmic measurement system. Pupil plane imaging provides a real image of the pupil and accommodates variability in the location, size and shape of a human pupil when making aberrometer measurements, especially because the location of a patient's eye is generally not well controlled. Pupil Plane Imaging is also beneficial in resolving the phase of a speckled beam, or a wavefront having one or more discontinuities.

Also beneficially, PDWS 300 may employ telecentric imaging. Telecentric imaging provides equally spaced sample planes, and provides equal magnification for all images. Telecentric imaging simplifies the alignment, calibration, and data processing of PDWS 300. Further details of the telecentric arrangement will be provided below.

Figure 13A:
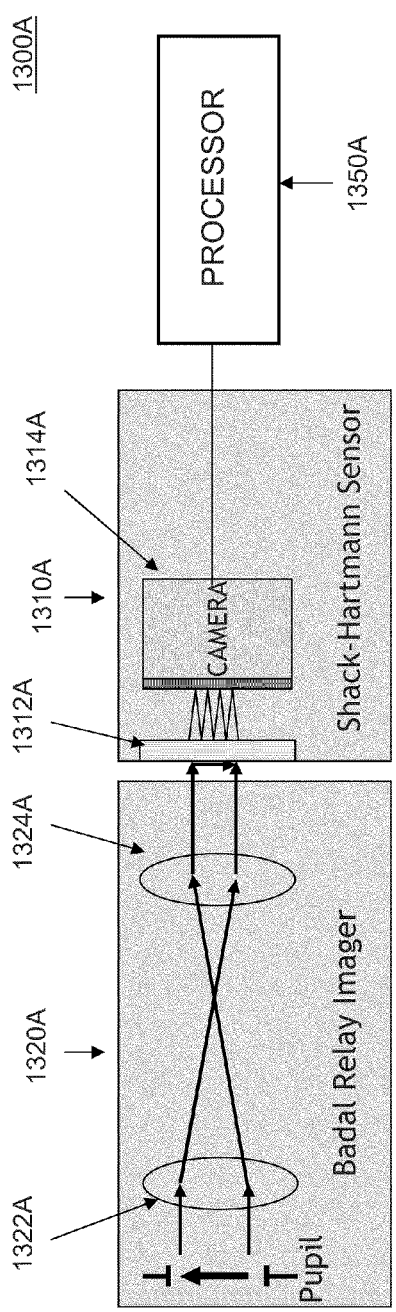
FIGS. 13A-C illustrate basic ophthalmic aberrometer designs for SHWS and PDWS sensors.
Figure 13B:
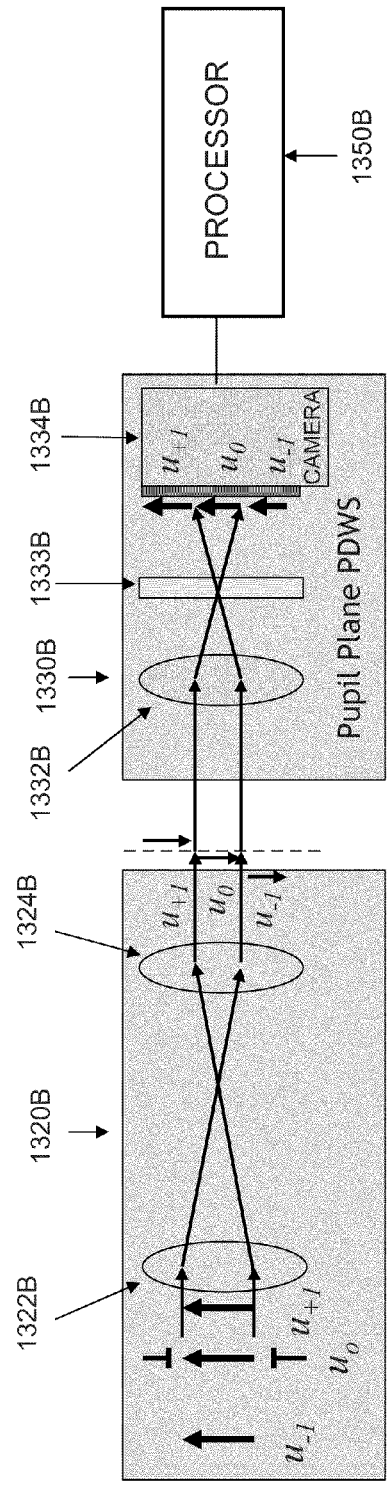
Figure 13C:
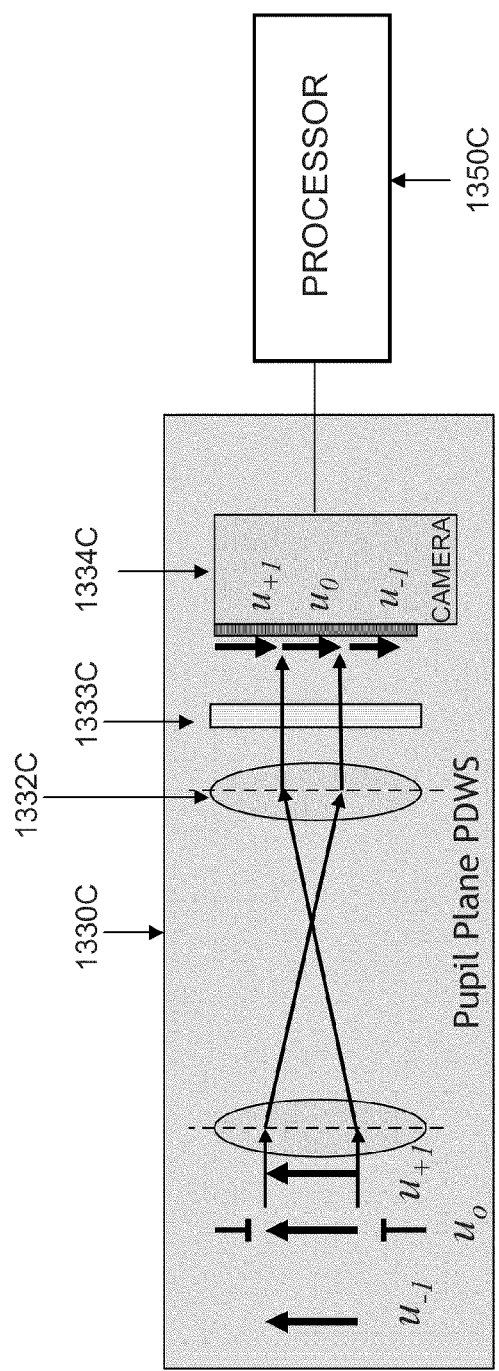

FIGS. 13A-C illustrate basic ophthalmic aberrometer designs for SHWS and PDWS sensors. Although not shown in FIGS. 13A-C, in practice the ophthalmic aberrometer will include a light projection system for creating the light beam and directing it to an eye or other object that is being measured. For example, the wavefront $\mu_o$ may be an image of a wavefront at a pupil or corneal surface of an eye under examination.

FIG. 13A illustrates an exemplary design for an ophthalmic aberrometer 1300A employing a SHWS 1310A. SHWS 1310A includes a lenslet array 1312A and a camera, or pixel array 1314A, also called a detector array. The design employs a Badal Relay Imager 1320A including two lenses 1322A and 1324A. A processor 1350A processes data produced by camera 1314A.

With the SHWS 1310A, both the spatial resolution and the dynamic range are correlated to the dimension of the lenslets in lenslet array 1312A. The optical system typically demagnifies the pupil image to fit on SHWS 1310A and the distance between lenses 1322A and 1324A is adjusted to add defocus to compensate the incoming wavefront so that it lies within the dynamic range of SHWS 1310A. Preservation of the optical phase front is important with SHWS 1310A, and image quality is generally a secondary consideration in the optical design. The sensitivity of SHWS 1310A is set by the lenslet focal length and the pixel size in camera 1314A and is adjusted to give a predetermined sensitivity. The sensitivity and spatial resolution requirements typically limit the dynamic range of SHWS 1301A to a few diopters. However, in aberrometer 1300A, the system can be dynamically adjusted to produce a larger effective dynamic range by moving one or both of the lenses 1322A and 1324A.

FIG. 13B illustrates an exemplary design for an ophthalmic aberrometer 1300B where a PDWS 1330B replaces the SHWS 1310A of FIG. 13A. PDWS 1330B includes lens 1332B, diffraction grating 1333B and camera, or pixel array 1334B, also called a detector array. A processor 1350B processes data produced by camera 1334B.

However, the arrangement of aberrometer 1300B is unnecessarily complex. Indeed, an analysis of the paraxial equations shows that telecentric imaging conditions can be specified, but the sample plane locations of the ±1 orders and the constrained location of diffraction grating 1333B are all non-linearly related to the spacing between lenses 1322B and 1324B. Adjustment of Badal Relay Imager 1320B hence requires complex adjustment of the position of diffraction grating 1333B. This suggests that such adjustment is not necessary, and indeed, significantly it suggests that Badal Relay Imager 1320B can be omitted.

FIG. 13C illustrates an exemplary design for an ophthalmic aberrometer 1300C is tailored for PDWS 1330C. Aberrometer 1330C includes lens 1332C, diffraction grating 1333C and camera, or pixel array 1334C, also called a detector array. A processor 1350C processes data produced by camera 1334C. By taking advantage of the large native dynamic range of PDWS 1330C, and the fact that it is essentially a multiplane imager, the part count can be reduced and the moving parts found in FIGS. 13A-B can be eliminated.

Accordingly and beneficially, ophthalmic aberrometer 1300C provides a comparable dynamic range to that of 1300A, yet requires no moving elements. That is, the positional relationship between all optical elements in ophthalmic aberrometer 1300C remains constant.

Turning again to FIG. 3, as noted above, beneficially PDWS 300 employs telecentric imaging. A generalized design procedure will now be explained for an aberrometer including PDWS 300 so as to provide the desired telecentric imaging.

Figure 14:
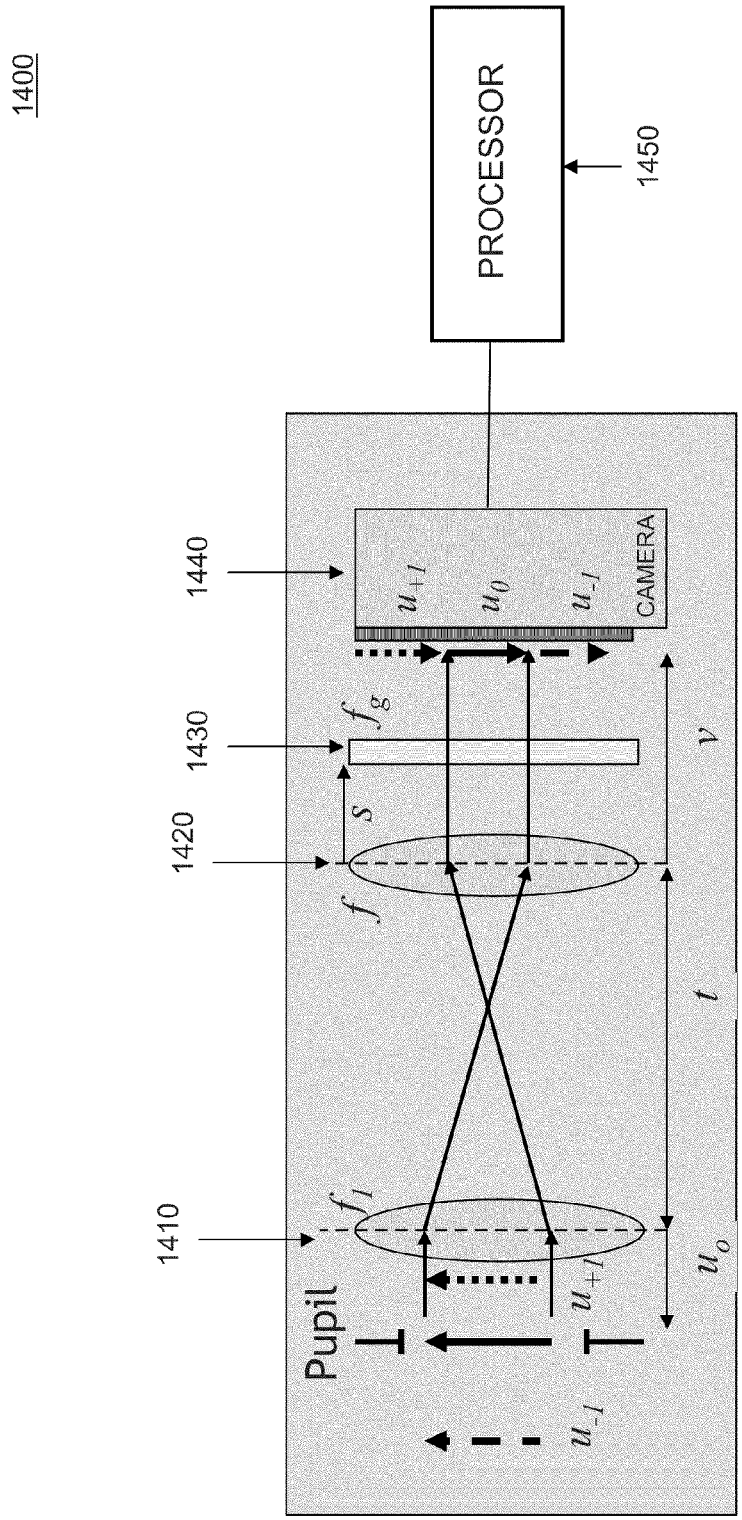
FIG. 14 illustrates a simplified design of a PDWS with a large dynamic range.

FIG. 14 illustrates a simplified design of a PDWS with a large dynamic range. FIG. 14 shows a first lens 1410, a second lens 1420, a diffraction grating 1430, a camera 1440, and a processor 1450. Analytic solutions with Pupil Plane and Telecentric Imaging and the use of static optical elements will be explained with respect to FIG. 14.

In one embodiment, an analytic solution is performed for the paraxial equations that govern the particular optical configuration of interest, using ray matrix analysis, to determine the proper arrangement to provide telecentric imaging. By first solving the paraxial equations analytically, the telecentric solution can be found by imposing the appropriate constraints on the general imaging solution; these constraints select the subset of the general paraxial imaging solutions with magnification independent of grating order, or equivalently, object positions that depend purely linearly on grating order. In one exemplary but non-limiting embodiment, the object plane locations for all images depend linearly on the grating order and the image magnifications are independent of the grating order for an optical configuration consisting of two lenses followed by a grating as shown in FIG. 13C. The lens focal lengths are respectively $f_1$ and $f$, the grating focal length in first order is $f_g$, m is the grating order, s is the distance between the second lens and the grating, t is the distance between the lenses and v is the space between the second lens and the detector array. Equation 5 shows the general solution for the telecentric pupil plane Lens-Lens-Grating PDWS.

$$s = f - \frac{f^2}{f - t + f_1} \quad (5)$$

$$u_m = \frac{(-tv + f(t+v))f_1}{-tv + f(t+v) + (-f+v)f_1} - \frac{f^2 m f_1^2}{(f-t+f_1)^2 f_g}$$

$$Mag = -\frac{v(f-t+f_1)}{f f_1}$$

The general telecentric pupil plane imaging PDWS equations shown above describe a family of solutions in which s, v and t are related for a given set of lens and grating focal lengths. Table 1 below shows representative examples of the family of analytic paraxial solutions for the Lens-Lens-Grating configuration of FIG. 14, derived using a symbolic manipulator (e.g., MATHEMATICA®) as shown in Equation 5, that provide both telecentric and pupil plane imaging for static lens positions for specific values of t and v. The sample plane locations $\mu_M$ (e.g., $\mu_{-1}$, $\mu_0$, $\mu_{+1}$) are linear in grating order, m, and the magnification is independent of grating order, characteristics of a telecentric imaging system. Note that the solution with $t=f_1$ is a telecentric pupil plane PDWS where the second lens and grating co-located; although this looks similar to the image plane sensor, the judicious positioning of each optical element provides the additional functionality of the pupil plane PDWS.

TABLE 1

| $t = f_1$ | $t = f$ | $t = f = v$ |
|---|---|---|
| $s = 0$ | $s = f - \dfrac{f^2}{f_1}$ | $s = f - \dfrac{f^2}{f_1}$ |
| $u_m = f_1\left(1 - \dfrac{f_1}{f} + \dfrac{f_1}{v}\right) - \dfrac{m f_1^2}{f_g}$ | $u_m = f^2\left(\dfrac{f_1}{f^2 + \dfrac{(-f+v)f_1}{}} - \dfrac{m}{f_g}\right)$ | $u_m = f_1 - \dfrac{f^2 m}{f_g}$ |
| $Mag = -\dfrac{v}{f_1}$ | $Mag = 1 - \dfrac{v}{f} - \dfrac{f}{f_1}$ | $Mag = -\dfrac{f}{f_1}$ |

Figure 15:
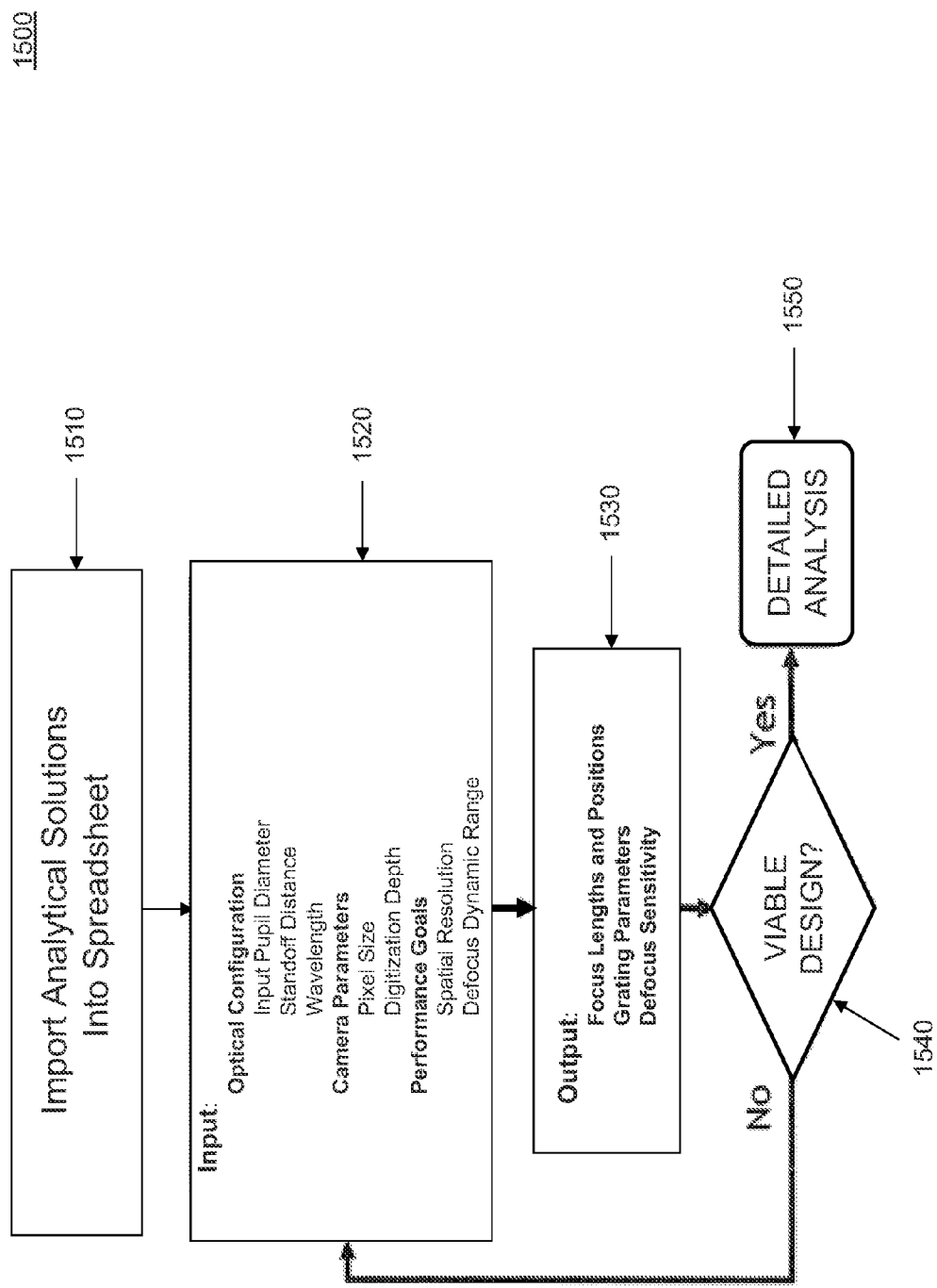
FIG. 15 illustrates a process of designing a measurement system that includes a PDWS.

FIG. 15 illustrates a process 1500 of designing a measurement system that includes a PDWS.

In a first step 1510, the analytical solutions are imported into a spreadsheet to explore the performance of the system versus input design parameters.

Then, in a step 1520, input design parameters are provided. The inputs may include the optical configuration, the location of the pupil plane, the desired dynamic range.

In a step 1530, outputs are generated based on the analytical solutions and the input design parameters. Outputs may include sensitivity, system length, actual dynamic range, etc.

In a step 1540, it is determined whether a viable design has been produced. If not, then the process returns to step 1520 and new input parameters are provided. If a viable deign has been achieved, then a detailed analysis is performed in step 1550.

Figure 16:
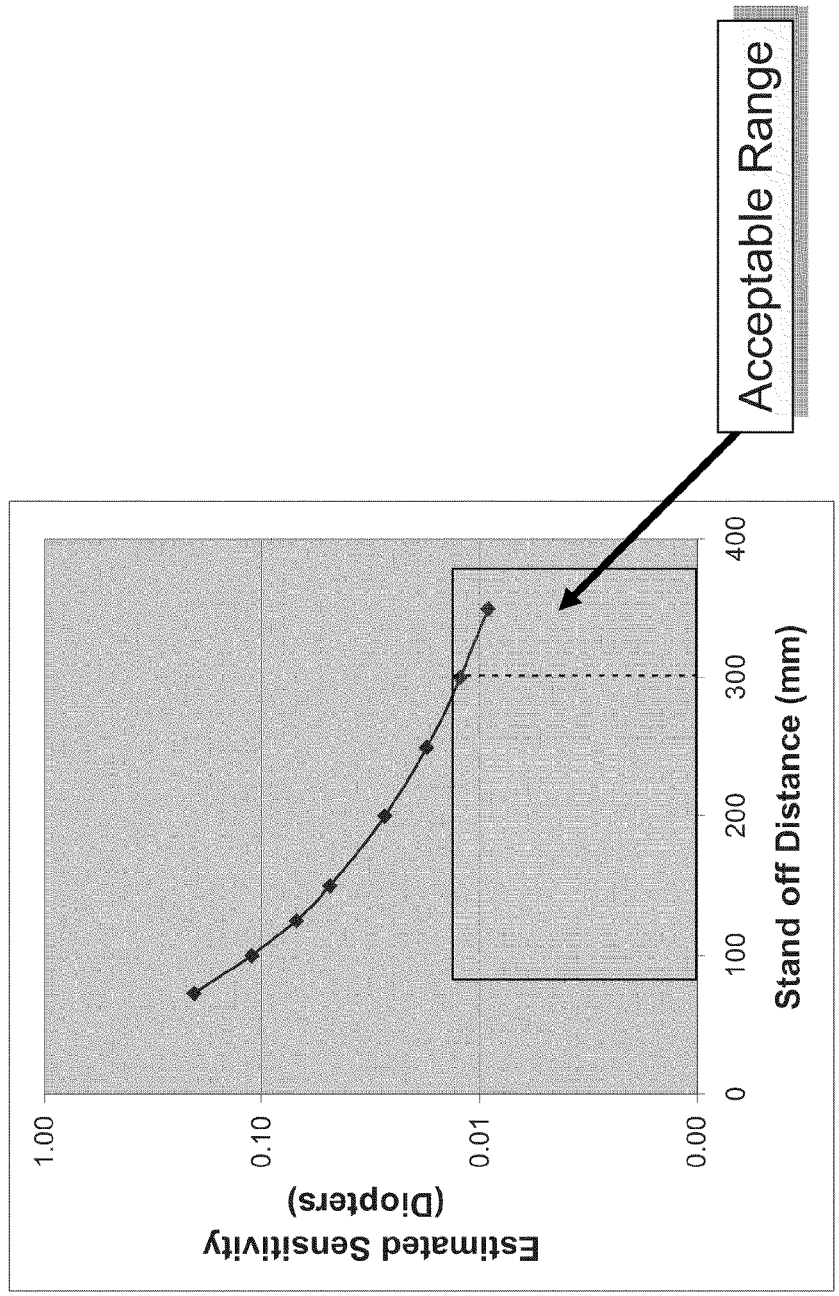
FIG. 16 illustrates how the process of FIG. 15 establishes design tradeoffs by comparing design points.

FIG. 16 illustrates how the process of FIG. 15 establishes design tradeoffs by comparing design points. FIG. 16 plots sensitivity versus pupil plane location. So, for example, if the system requires a sensitivity of at least 0.01 diopters and a stand-off distance between 73 and 375 mm, as illustrated in FIG. 16, an acceptable performance range exists and final detailed ray matrix analysis of this system configuration is warranted as it is a viable design. This design method is beneficial in assisting in the early rejection of candidate configurations before significant investment is made in their detailed analysis; in contrast, traditional design methods do not permit the elimination of such unviable candidate configurations without the expense of a detailed ray matrix analysis.

Figure 17:
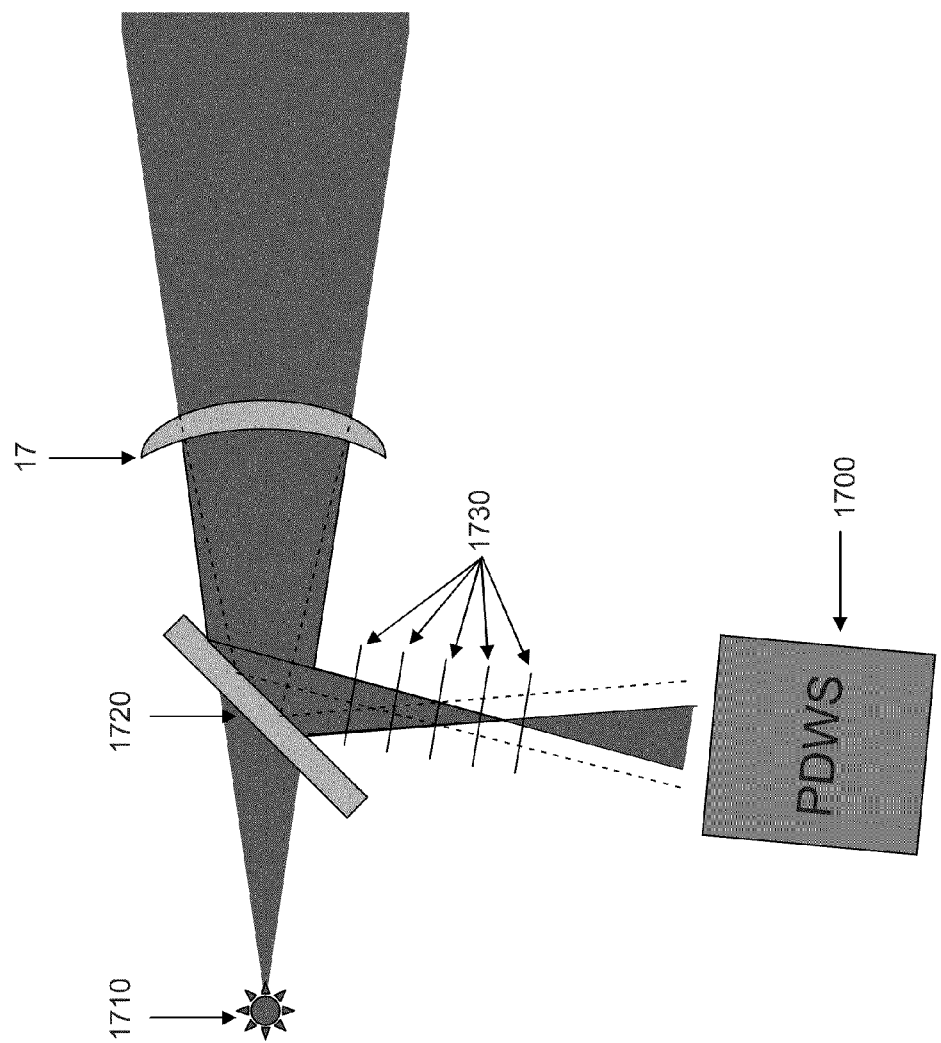
FIG. 17 illustrates how a PDWS can be used to measure both surfaces of a contact lens.

FIG. 17 illustrates how a PDWS 1700, such as PDWS 300 or PDWS 1400, can be used to measure both surfaces of a lens 17, for example, a contact lens or an intraocular lens. Light from a light source 1710 is passed through a beamsplitter 1720 to lens 17. Reflections are produced from both surfaces of lens 17 and pass back through beamsplitter to the PDWS 1700 which has sample planes located about the focal positions of the light reflected from the two lens surfaces. Here, the advantages of PDWS 1700 can be seen. For example, if a SHWS were employed in this application, the multiple reflections from the surfaces of lens 17 would generate multiple focal spots from its lenslet array that could confuse the processor associated with a SHWS. In contrast, PDWS 1700 can easily distinguish between the two reflected wavefronts, and therefor both surfaces of lens 17 can be characterized. In this example, the wave reflected from each surface will focus at different distances from the lens; it is obvious that by suitably placing sufficient PDWS sample planes near these foci, sufficient data can be made available to a Gerchberg-Saxton phase retrieval algorithm to determine the wavefront from each surface and hence the optical effect of each surface. More than two sample planes may be required in such multi wavefront applications and their number and locations may be expected to affect the accuracy of the phase retrieval. Generally the greater the number of sample planes the greater the accuracy of the phase retrieval; likewise, judiciously placing the sample planes around the locations where the intensities contributed at those planes by the various wavefronts are most disparate will lead to the greatest accuracy in retrieving each component in the multi wavefront.

Figure 18A:
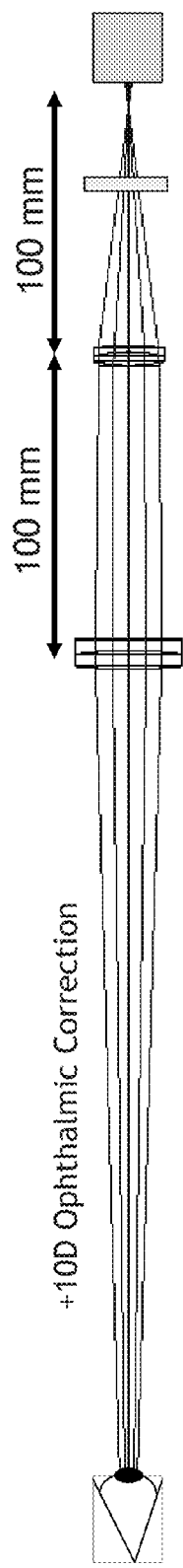
FIGS. 18A-C illustrate the use of a PDWS in an ophthalmic measurement application.
Figure 18B:
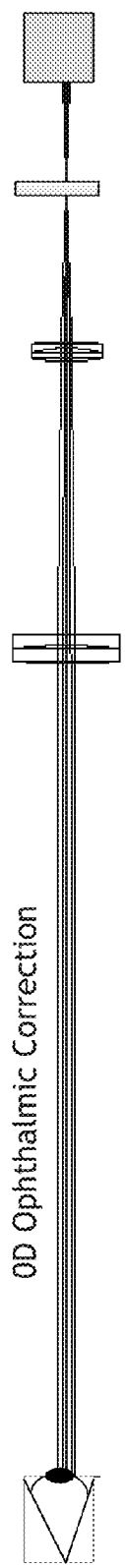
Figure 18C:
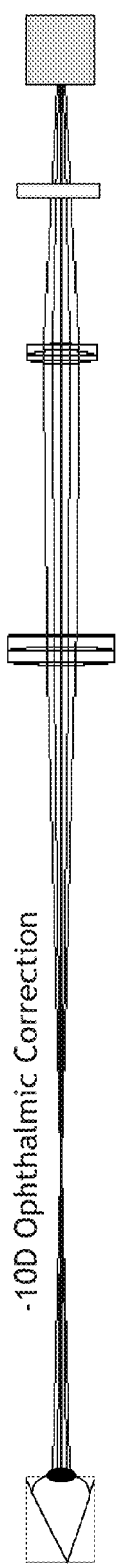

FIGS. 18A-C illustrate the use of a PDWS in an ophthalmic measurement application. FIGS. 18A-C show ray trace results from a non-paraxial analysis. The PDWS configuration illustrated in FIGS. 18A-C has a 300 mm pupil plane (standoff) distance, and the camera has 300 pixels across a width of 6 mm. Other parameters include: first lens with f=100 mm and 25 mm dial.; second lens with $f_1$=300 mm and 38 mm dia.; DOE with $f_g$=500 mm and 9 μm center grating period. FIG. 18A illustrates a case where +10 diopters of ophthalmic correction are required; FIG. 18B illustrates a case where 0 diopters of ophthalmic correction are required; and FIG. 18C illustrates a case where −10 diopters of ophthalmic correction are required. The ray trace analysis shown in FIGS. 18A-C shows that light rays are fully transmitted to the camera in this arrangement for beams within the range ±10 diopters of defocus; for this reason, this configuration is suitable to acquire the data necessary to analyze beams with this wide range of defocus. Indeed even larger ranges may be possible by increasing the diameter of the second lens. The fact that the second lens is quite nearly filled by the rays in the +10 diopter case suggests that some non paraxial behavior may be expected in this limit. The detailed ray trace analysis of such a system employing realistic commercially available lenses shows that the non-paraxial behavior of the system magnification departs from ideal by only about 1.3% at the extremes of the dynamic range, well within the acceptable tolerance for an ophthalmic aberrometer.

Figure 19:
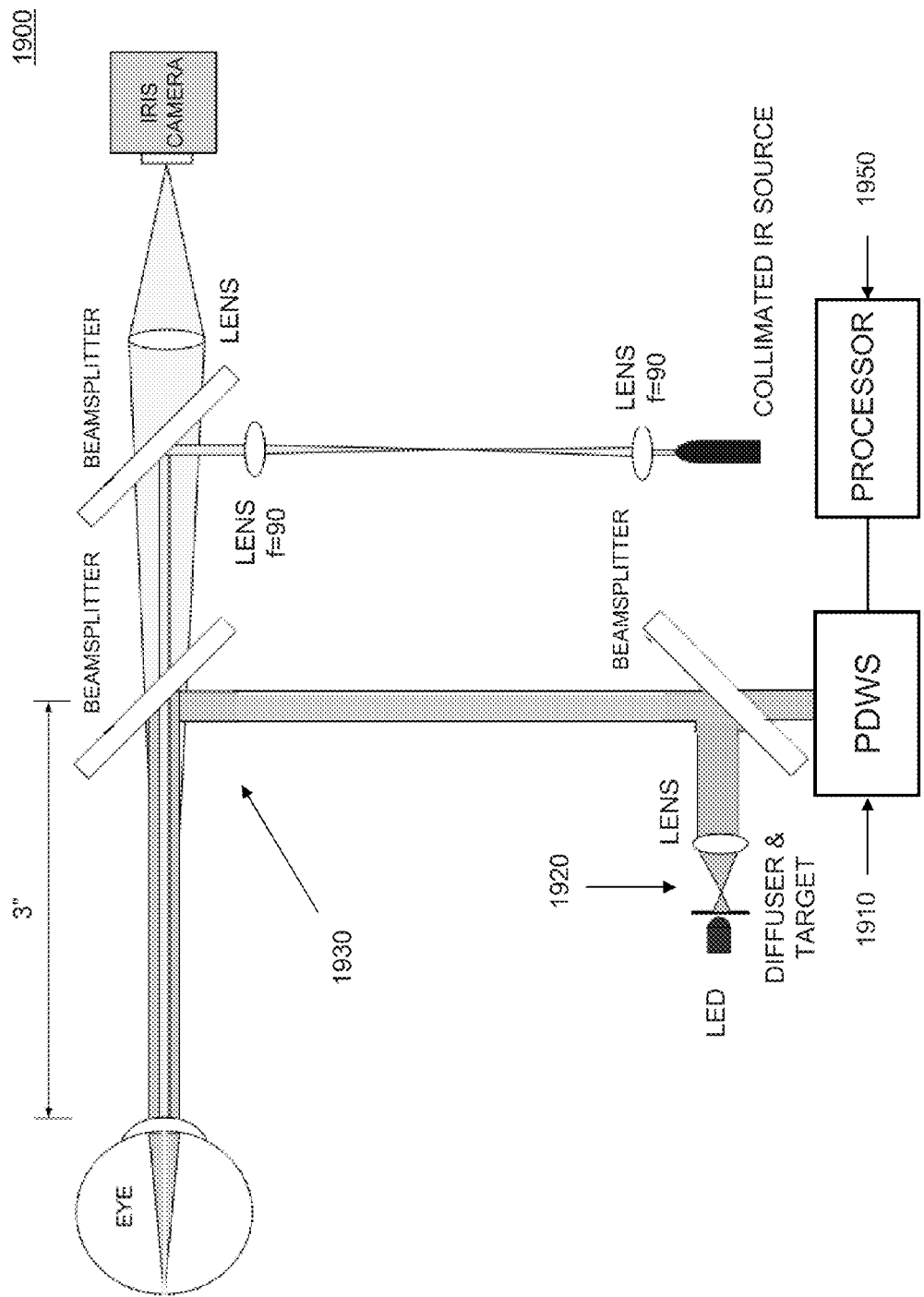
FIG. 19 illustrates a block diagram of one embodiment of an ophthalmic aberrometer that includes a PDWS.

FIG. 19 illustrates a block diagram of one embodiment of an ophthalmic aberrometer 1900 that includes a PDWS 1910, which for example can be PDWS 300 or PDWS 1400. Ophthalmic aberrometer 1900 also includes a light source 1920, an optical system 1930, and a processor 1950.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A phase diversity wavefront sensor, comprising:
an optical system including at least one optical element for receiving a light beam having a diameter greater than about 1.5 mm and comprising one or more aberrations;
a diffractive optical element having a diffractive pattern defining a filter function, the diffractive optical element being arranged to produce, in conjunction with the optical system, images from the light beam associated with at least two diffraction orders, the images corresponding to at least two or more sample planes, the one or more aberrations altering a size of the light beam between the sample planes;
a detector for detecting the images at a measurement plane and outputting image data corresponding to the detected images, wherein the optical system, diffractive optical element, and detector are arranged to provide telecentric, pupil plane images of the light beam such that real images are formed at the sample planes and the measurement plane; and
a processor coupled to the detector and configured to receive the image data, the processor executing a phase retrieval algorithm to measure a wavefront of the light beam based on the images corresponding to the sample planes.

2. The phase diversity wavefront sensor of claim 1, wherein the filter function is quadratic.

3. The phase diversity wavefront sensor of claim 1, wherein the filter function is non-quadratic and has non-mixed symmetry.

4. The phase diversity wavefront sensor of claim 1, wherein the diffractive optical element is a diffraction grating.

5. The phase diversity wavefront sensor of claim 1, wherein the processor executes a Gerchberg-Saxton phase retrieval algorithm to measure the wavefront of the light beam.

6. The phase diversity wavefront sensor of claim 1, wherein the optical system includes a plurality of optical elements all having fixed positional relationships to the diffractive optical element and the detector.

7. The phase diversity wavefront sensor of claim 1, wherein none of the optical elements in the optical system are adjustable.

8. The phase diversity wavefront sensor of claim 1, wherein the at least one optical element is at least one of a lens, a mirror, or a second diffractive optical element.

9. The phase diversity wavefront sensor of claim 1, wherein the at least one optical element and the diffractive optical element are combined into a single optical element.

* * * * *